United States Patent [19]

Doussain et al.

[11] Patent Number: 5,132,468

[45] Date of Patent: Jul. 21, 1992

[54] C-ALKYLATION OF HYDROQUINONE OR MONOETHERS THEREOF

[75] Inventors: Claude Doussain, Saint-Fons; Michel Gubelmann, Lyons; Philippe-Jean Tirel, Oullins, all of France

[73] Assignee: Rhone-Poulenc Chimie, Courbevoie, France

[21] Appl. No.: 643,181

[22] Filed: Jan. 18, 1991

[30] Foreign Application Priority Data

Jan. 19, 1990 [FR] France ............... 90 00814

[51] Int. Cl.$^5$ .................. C07C 37/20; C07C 39/08
[52] U.S. Cl. .................. 568/766; 568/763; 568/804
[58] Field of Search ............ 568/766, 763, 804, 784, 568/790

[56] References Cited

U.S. PATENT DOCUMENTS 2,296,363  9/1942  Messer .................. 568/766
2,510,937  6/1950  Tadema ................. 568/766

FOREIGN PATENT DOCUMENTS 0264751  10/1985  Japan .................... 568/766
10-07226  1/1986  Japan .................... 568/766

Primary Examiner—Werren B. Lone
Attorney, Agent, or Firm—Burns, Doane, Swecker & Mathis

[57] ABSTRACT

The alkyl hydroquinones, e.g., methyl hydroquinone (a useful intermediate in the preparation of the monomer methyl hydroquinone diacetate, itself used for the synthesis of thermotropic polymers), are prepared by reacting (C-alkylating) hydroquinone or a monoether thereof with a lower alkanal, in the vapor phase, with a catalytically effective amount of at least one solid metal oxide.

22 Claims, No Drawings

C-ALKYLATION OF HYDROQUINONE OR MONOETHERS THEREOF

BACKGROUND OF THE INVENTION

1. Field of the Invention

The present invention relates to the C-alkylation of hydroquinone or monoethers thereof, and, more especially, to such C-alkylation by vapor phase reaction with an alkanal in the presence of a solid catalyst.

2. Description of the Prior Art

Among the alkyl hydroquinones, a particularly desirable compound is methyl hydroquinone, which is used for preparing methyl hydroquinone diacetate, a valuable monomer used for the synthesis of thermotropic polymers.

A variety of processes are known to this art for preparing methyl hydroquinone. For example, U.S. Pat. No. 2,041,593 describes the hydrolysis of 4-chloro-2-methylphenol into methyl hydroquinone in an aqueous sodium medium. EP-A-1,441 describes the hydroxylation of orthocresol in hydrogen fluoride at $-40°$ C., in the presence of antimony pentafluoride. U.S. Pat. No. 4,482,756 describes the oxidation of orthocresol by oxygen, in the presence of cupric chloride in acetonitrile.

SUMMARY OF THE INVENTION

A major object of the present invention is the provision of a novel process for the preparation of alkyl hydroquinones from hydroquinone or monoethers of hydroquinone.

Briefly, the present invention features reacting hydroquinone or one of the alkyl monoethers thereof having from 1 to 4 carbon atoms, or a cyclohexyl monoether thereof, with a lower alkanal, in the vapor phase, in the presence of a catalytically effective amount of at least one solid metal oxide.

DETAILED DESCRIPTION OF THE PREFERRED EMBODIMENTS OF THE INVENTION

More particularly according to the present invention, when a hydroquinone monoether starting material is used, it is advantageously a methyl, ethyl, isopropyl or cyclohexyl monoether.

As utilized herein, by the term "diphenol" are intended hydroquinone and the aforesaid monoethers thereof. By the term "lower alkanal" are intended aldehydes derived from alkanes having from 1 to 4 carbon atoms. Exemplary such alkanals include methanal or formaldehyde, ethanal or acetaldehyde, propanal or butanal. Methanal is the preferred such alkanal.

Methanal can be used in the form of gaseous formaldehyde, an aqueous formaldehyde solution, or in solid polymerized form such as 1,3,5-trioxane.

The metal oxides used as catalysts in the process according to the invention can be single or mixed, acid, amphoteric or basic oxides, or mixtures of these different oxides.

Among the oxides generally considered as acidic or amphoteric, representative are the single oxides such as silicon oxide (silica), aluminum oxide (alumina), titanium dioxide, zirconium dioxide, stannic oxide, arsenous oxide, lead (II) oxide, bismuth (III) oxide, vanadium (V) oxide, antimony (V) oxide, thorium dioxide, chromium (VI) oxide and molybdenum (VI) oxide.

Among the oxides generally considered as basic, particularly representative are magnesium oxide, lanthanum oxide, zinc oxide, chromium (III) oxide, copper (II) oxide and aluminum oxide (alumina).

And exemplary of the mixed oxides are the zeolites or molecular sieves in the form of silicoaluminates, particularly in their alkali metal silicoaluminate form and preferably sodium or cesium silicoaluminates. Faujasite-type zeolites are particularly suitable.

The lower alkanal/diphenol molar ratio can vary widely and typically ranges from 0.05 to 10. Preferably, the lower alkanal/diphenol molar ratio ranges from 0.5 to 5.

The process according to the invention is typically carried out at a temperature ranging from 200° to 500° C, provided that the diphenol employed is in the vapor state. Preferably, the reaction temperature ranges from 300° to 450° C.

In this preferred temperature range, which is in general suitable for all metal oxides, it is even more preferred to conduct the reaction in temperature ranges adapted to the metal oxide used as the catalyst. Thus, the process is preferably carried out at temperatures ranging from 300° to 350° C. when the catalyst is an amphoteric or acid metal oxide, and at temperatures ranging from 350° to 450° C. when the catalyst is a basic metal oxide.

The reaction is advantageously carried out continuously in a tubular reactor, wherein the solid catalyst is arranged in fixed bed form.

The catalyst can be in different forms, e.g., powder, particularly for laboratory tests, or shaped articles such as granules (e.g., cylinders), spheres, pellets or monoliths (honeycomb-shaped blocks) produced by extrusion, molding, compacting, or any other known process.

The diphenol and alkanal can be introduced separately or in mixed form into the reactor. They can also be introduced together with an inert diluent, which is a solvent for the diphenol and alkanal.

Exemplary such solvents are water and ethers. Among the ethers, particularly representative are the dimethyl or diethyl ethers derived from ethylene oxide or propylene oxide, such as ethylene glycol dimethyl ether (or 1,2-dimethoxyethane), ethylene glycol diethyl ether (or 1,2-diethoxyethane), 1,5-dimethoxy-3-oxapentane, 1,5-diethoxy-3-oxapentane, 1,8-dimethoxy-3,6-dioxaoctane, 1,11-dimethoxy-3,6,6-trioxaundecane, 1,2-dimethoxy-1-methylethane, 1,5-dimethoxy-1,4-dimethyl-3-oxapentane and 1,8-dimethoxy-1,4,7-trimethyl-3,6-dioxaoctane.

It is also possible to use several solvents, such as, e.g., a mixture of water and an ether, as defined hereinbefore.

It is generally advantageous to use a vector gas such as nitrogen or hydrogen or a mixture of these two gases, in order to facilitate the transfer of the reagents into the reactor.

The contact time with the catalyst can be expressed by the ratio between the overall flow rate (by volume/time unit) and the catalyst volume of the reaction. temperature. The contact time generally ranges from approximately 0.1 to 10 seconds.

It is also possible to utilize the concept of productivity, which is expressed by the reagent weight quantity introduced by catalyst weight per unit of time.

In order to further illustrate the present invention and the advantages thereof, the following specific examples are given, it being understood that same are intended only as illustrative and in nowise limitative.

In said examples to follow, the tests were carried out in a vertical, Pyrex glass, tubular reactor having an internal diameter of 15 mm and an internal volume of 20 cc, equipped in its upper part with a lateral intake for the supply of liquid fluids and an intake for the central supply of gaseous fluids, together with a central sheath having an internal diameter of 5 mm for receiving the thermocouples.

The lower part of the reactor was provided with a fritted glass disk for supporting the catalyst, while permitting the passage of the fluids therethrough.

In the reactor were successively arranged, from bottom to top:

(i) a 1 cc glass powder layer (grain size 2 mm);

(ii) a layer constituted by the mixture of 3 cc of catalytic metal oxide (having a grain size of 0.8 to 1.25 mm) and 6 c of glass powder (grain size 2 mm);

(iii) a 2 cc glass powder layer (grain size 2 mm).

The above constituted the catalytic bed.

It was also provided with means for heating the catalytic bed.

EXAMPLES 1 TO 5

In the above reactor were carried out various tests using the metal oxides indicated in the following Table. These metal oxides were utilized in the manner described hereinbefore.

The catalytic bed was heated at 440° C. for 60 minutes and then, while maintaining a temperature of 440° C., using a push syringe and a flow rate of 4.37 g/hour, a solution was injected into the reactor prepared from 2.75 g (25 mmole) of hydroquinone, 3 g (100 mmole) of 1,3,5-trioxane, 0.45 g (25 mmole) of water and 122 g (75 mmole) of diethylene glycol diethyl ether.

Except in Example 5, where the vector gas was nitrogen, hydrogen was also introduced at a flow rate of 1.05 liter/hour (volume calculated under normal conditions of temperature and pressure).

The operation was carried out in this manner for 30 minutes to establish the equipment operating conditions and then for the following 60 minutes the reaction mixture exiting the reactor was trapped and analyzed by vapor phase chromatography and mass spectrometry. The contact time, as defined above, was 2 seconds for each of the tests.

A control test was carried out under the same conditions, but the reactor then contained only the glass powder (total volume 12 cc).

The following Table reports the results obtained.

TABLE

| TESTS | CATALYST | TT % HQ | RT % MeHQ | RT % Me2HQ | RT % MeBZQ |
|---|---|---|---|---|---|
| Control | glass spheres | 10 | 1 | 0 | 0 |
| Example 1 | $Cr_2O_3$ | 42 | 51 | 4 | 4 |
| Example 2 | $Zr_2O_3$ | 40 | 46 | 3 | 3 |
| Example 3 | $La_2O_3$ | 61 | 29 | 10 | 1 |
| Example 4 | MgO | 60 | 31 | 7 | 0 |
| Example 5 | MgO | 61 | 29 | 6 | 0 |

Abbreviations used in the Table:
TT & HQ: Degree of conversion (in %) of hydroquinone.
RT % MeHQ: Methyl hydroquinone yield compared with hydroquinone converted.
RT % Me2HQ: Dimethyl hydroquinone yield compared with hydroquinone converted.
RT % MeBZQ: Methyl benzoquinone yield compared with hydroquinone converted.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the C-alkylation of hydroquinone or monoether thereof, comprising reacting such hydroquinone or monoether thereof with an alkanal, in the vapor phase, in the presence of a catalytically effective amount of at least one solid metal oxide.

2. The process as defined by claim 1, comprising reacting a methyl, ethyl, isopropyl or cyclohexyl monoether of hydroquinone with a lower alkanal.

3. The process as defined by claim 1, said alkanal comprising methanal, ethanal, propanal or butanal.

4. The process as defined by claim 3, said alkanal comprising methanal.

5. The process as defined by claim 1, said at least one metal oxide comprising an amphoteric, basic or acidic metal oxide.

6. The process as defined by claim 5, said at least one metal oxide comprising silica, alumina, titanium dioxide, zirconium dioxide, stannic oxide, arsenous oxide, lead (II) oxide, bismuth (III) oxide, vanadium (V) oxide, antimony (V) oxide, thorium dioxide, chromium (VI) oxide or molybdenum (VI) oxide.

7. The process as defined by claim 5, said at least one metal oxide comprising magnesium oxide, lanthanum oxide, zinc oxide, chromium oxide, copper oxide or alumina.

8. The process as defined by claim 5, said at least one metal oxide comprising a zeolite or molecular sieve.

9. The process as defined by claim 8, said zeolite or molecular sieve comprising an alkali metal silicoaluminate.

10. The process as defined by claim 9, said alkali metal comprising sodium or cesium.

11. The process as defined by claim 8, said at least one metal oxide comprising a zeolite of faujasite type.

12. The process as defined by claim 1, wherein the alkanal/diphenol molar ratio ranges from 0.05 to 10.

13. The process as defined by claim 12, said molar ratio ranging from 0.5 to 5.

14. The process as defined by claim 1, carried out at a temperature ranging from 200° to 500° C.

15. The process as defined by claim 14, carried out at a temperature ranging from 300° to 450° C.

16. The process as defined by claim 1, carried out continuously in a tubular reactor, said at least one metal oxide comprising a fixed bed therein.

17. The process as defined by claim 16, comprising separately introducing said diphenol and alkanal into said reactor.

18. The process as defined by claim 16, comprising introducing admixture of said diphenol and alkanal into said reactor.

19. The process as defined by claim 16, comprising introducing an inert solvent solution of said diphenol and alkanal into said reactor.

20. The process as defined by claim 19, said solvent comprising an ether or water.

21. The process as defined by claim 20, said solvent comprising ethylene glycol dimethyl ether (1,2-dimethoxy ethane), ethylene glycol diethyl ether (1,2-diethoxy ethane), 1,5-dimethoxy-3-oxapentane, 1,5-diethoxy-3-oxapentane, 1,8-dimethoxy-3,6-dioxaoctane, 1,11-dimethoxy-3,6,9-trioxaundecane, 1,2-dimethoxy-1-methylethane, 1,5-dimethoxy-1,4-dimethyl-3-oxapentane or 1,8-dimethoxy-1,4,7-trimethyl-3,6-dioxaoctane.

22. The process as defined by claim 16, comprising introducing said diphenol and alkanal into said reactor while entrained in a vector gas therefor.

* * * * *